(12) United States Patent
Schulze-Ganzlin

(10) Patent No.: US 11,957,494 B2
(45) Date of Patent: Apr. 16, 2024

(54) METHOD FOR PREPARING AN X-RAY IMAGE, METHOD FOR TAKING AN X-RAY IMAGE, DEVICE FOR DATA PROCESSING, COMPUTER PROGRAM PRODUCT, MEDIUM AND X-RAY MACHINE

(71) Applicant: DENTSPLY SIRONA INC., York, PA (US)

(72) Inventor: Ulrich Schulze-Ganzlin, Lorsch (DE)

(73) Assignee: DENTSPLY SIRONA INC., York, PA (US)

( * ) Notice: Subject to any disclaimer, the term of this patent is extended or adjusted under 35 U.S.C. 154(b) by 413 days.

(21) Appl. No.: 17/311,412

(22) PCT Filed: Dec. 9, 2019

(86) PCT No.: PCT/EP2019/084273
§ 371 (c)(1),
(2) Date: Jun. 7, 2021

(87) PCT Pub. No.: WO2020/120413
PCT Pub. Date: Jun. 18, 2020

(65) Prior Publication Data
US 2022/0022828 A1    Jan. 27, 2022

(30) Foreign Application Priority Data
Dec. 10, 2018    (EP) .................................... 18211402

(51) Int. Cl.
*A61B 6/14* (2006.01)
*A61B 6/00* (2006.01)
*A61B 6/08* (2006.01)
*A61B 6/46* (2024.01)

(52) U.S. Cl.
CPC ................. *A61B 6/145* (2013.01); *A61B 6/08* (2013.01); *A61B 6/466* (2013.01); *A61B 6/542* (2013.01)

(58) Field of Classification Search
CPC ........... A61B 6/145; A61B 6/08; A61B 6/466; A61B 6/542
See application file for complete search history.

(56) References Cited

U.S. PATENT DOCUMENTS 11,369,459 B2 *    6/2022    Kopelman ............... A61C 8/00

* cited by examiner

*Primary Examiner* — Hugh Maupin
(74) *Attorney, Agent, or Firm* — DENTSPLY SIRONA INC.

(57) ABSTRACT

The present invention relates to a method for preparing an X-ray image, which can be carried out by an X-ray machine, of at least one surface and/or volume area of at least one part of at least one head of at least one patient. The invention also relates to a corresponding device for data processing, a corresponding computer program product, a corresponding medium and a corresponding X-ray machine. The invention also relates to a method for taking an X-ray image which can be carried out by an X-ray machine of at least one surface and/or volume area of at least one part of at least one head of at least one patient.

15 Claims, 4 Drawing Sheets

METHOD FOR PREPARING AN X-RAY IMAGE, METHOD FOR TAKING AN X-RAY IMAGE, DEVICE FOR DATA PROCESSING, COMPUTER PROGRAM PRODUCT, MEDIUM AND X-RAY MACHINE

CROSS-REFERENCE TO RELATED APPLICATIONS

This is a National Phase application of International Application No. PCT/EP2019/084273 filed Dec. 9, 2019, which claims the benefit of and priority to European Patent Application Number EP18211402.5filed on Dec. 10, 2018 which are herein incorporated by reference for all purposes.

TECHNICAL FIELD

The present invention relates to a method for preparing an X-ray image, which can be carried out by an X-ray machine, of at least one surface and/or volume area of at least one part of at least one head of at least one patient. The invention also relates to a corresponding device for data processing, a corresponding computer program product, a corresponding medium and a corresponding X-ray machine. The invention also relates to a method for taking an X-ray image which can be carried out by an X-ray machine of at least one surface and/or volume area of at least one part of at least one head of at least one patient.

BACKGROUND OF THE INVENTION

For the preparation of 2D panorama images or 3D volume X-ray images in the maxillofacial area the patient has to be positioned correctly inside the X-ray machine. This includes correctly orientating and aligning as well as positioning the head of the patient relative to the X-ray machine. In this way it is ensured that the surface to be recorded or the volume to be recorded as the so-called Region of Interest (ROI) is indeed fully recorded, which is thus located in or coincides with the area illuminated by the X-ray machine (Field of View, FoV). From the perspective of the X-ray hygiene the area should not be too large, from the perspective of dental indication, it should not be too small.

In principle, the head of the patient is fixed mechanically by a head holder in a desired position, and/or aligned by means of a bite block device. Various ways of adjusting the location and position of the patient's head are already known from the prior art.

Thus from DE 10 2004 041 440 A1 a method is known for determining the target relative position of a patient in a dental panorama-X-ray machine. Here, the curvature of a front area of a dental arch of a patient is determined. From the latter and from a projection arched surface, target position coordinates for the patient are calculated. In addition, the curvature of a middle area and/or rear area of the dental arch is determined and taken into consideration for the calculation of the target position coordinates. To determine the tooth arch geometry it is proposed in particular to use two cameras fixed to the X-ray machine. This method has proved to be effective in general, but it also has been shown that the cameras in same circumstances only have a restricted viewpoint into the oral cavity, which can necessitate manual intervention to the working process.

Furthermore, it has already been proposed by means of a so-called initial "scout shot" to take a 2D image, by means of which it is possible to tell whether the area illuminated by the X-ray machine (FoV) matches the desired region of interest (ROI). While it is possible with this method to adjust the FoV very accurately to the desired ROI. However, an additional X-ray image with the accompanying X-ray exposure is necessary. Furthermore, the workflow is obstructed, as an evaluation of the "scout shot" and, if required, an adjustment of the FoV is necessary. These circumstances finally result in a much more complex, slower and not least also error-prone procedure.

Furthermore, it has also been proposed by means of light, in particular laser light targeting, to project the position of the FoV onto the head of the patient so that the operator of the X-ray machine can roughly estimate the course of the FoV by means of light projections. This procedure is possible without any additional radiation, however it has the disadvantage that an ROI located inside the head, in particular in the oral cavity, has to be estimated from external markings on the head. This procedure is therefore comparatively imprecise. Furthermore, the external laser light markings on the head of the patient might be depicted with a distortion on the patient's face, with the result that the FoV may be positioned incorrectly.

Reference is also made to US 2011/0129058 A1 which discloses a method of producing a dental 3D X-ray image, and x-ray device for the same.

SUMMARY OF THE INVENTION

Therefore, the objective of the present invention is to overcome the disadvantages of the prior art and provide solutions for this, to prepare or take an X-ray image, wherein the illumination area of the X-ray machine can be adjusted in a reliable, simple and mainly secure manner to the desired area of interest or the desired investigation volume.

This objective is achieved according to a first aspect of the invention by a method for preparing an X-ray image, which can be carried out by means of an X-ray machine of at least one surface and/or volume area of at least one part of at least one head of at least one patient, comprising the steps: receiving and/or processing first data with respect to at least one area of at least one first anatomical structure of the head and/or receiving and/or processing second data with respect to at least one area of at least one second anatomical structure of the head; calculating at least one first 3D structure at least of the area of the first anatomical structure on the basis of at least the first data and/or calculating at least one second 3D structure at least of the area of the second anatomical structure on the basis of at least the second data; aligning, positioning and/or arranging the first 3D structure and/or the second 3D structure within at least one coordinate system assigned and/or assignable to the X-ray machine; receiving and/or processing third data, by means of which the surface and/or volume area within the coordinate system is determined and/or determinable at least in some areas; and determining, on the basis of at least the third data at least one parameter for operating the X-ray machine and/or at least one movement unit comprised and/or comprisable by the X-ray machine.

It is particularly preferable that (i) the first anatomical structure comprises at least one first jaw, at least one first dental object and/or at least one midface, in particular at least one frontal sinus cavity; (ii) the second anatomical structure comprises at least one second jaw, at least one second dental object and/or at least the midface, in particular the frontal sinus cavity; (iii) the first jaw comprises and/or represents an upper jaw, the second jaw comprises and/or represents a lower jaw, in particular corresponding to the first jaw, the first dental object is arranged at least partly and/or at least in some areas in and/or on the first jaw, the second dental object is arranged at least partly and/or at least in some areas in and/or on the second jaw, the first dental object comprises at least one tooth, in particular of the first jaw, and/or the second dental object comprises at least one tooth, in particular of the second jaw; (iv) the third data (a) is predefined, in particular saved in a storage unit and is preferably retrieved from the latter, (b) is selected and/or can be selected by a user, in particular textually and/or graphically, and/or (c) is selected and/or can be selected by means of segmentation and/or artificial intelligence, in particular by a computer device; and/or (v) the parameter comprises and/or represents (a) setting data for setting at least one aperture, in particular comprised by the X-ray machine, (b) setting data for setting at least one dose of X-rays used by the X-ray machine and/or (c) movement data for performing at least one movement of the movement unit along at least one section of at least one movement trajectory within the coordinate system.

It can also be provided that (i) the first data and/or the second data are recorded and/or recordable by MRT, X-ray and/or at least one optical recording unit, in particular at least one intraoral camera, at least one laser-based measuring system and/or at least one camera, preferably at least one 3D camera; (ii) the first data comprises MRT data, X-ray data, optical image data, distance data, height data, reflection data, a virtual imprint and/or 3D data, in particular precalculated 3D data, with respect to the first anatomical structure, in particular the first jaw and/or the first dental object; (iii) the second data comprises MRT data, X-ray data, optical image data, distance data, height data, reflection data, a virtual imprint and/or 3D data, in particular precalculated 3D data, with respect to the second anatomical structure, in particular the second jaw and/or the second dental object; (iv) the first data comprises information on at least one surface, in particular at least one occlusal surface, of the first dental object and/or the first data comprises image data of at least the occlusal surfaces at least of half the side of the upper jaw of the patient; (v) the second data comprises information on at least one surface, in particular at least one occlusal surface, of the second dental object and/or the second data comprises at least image data of at least the occlusal surfaces of at least half the side of the lower jaw of the patient; (vi) the movement unit comprises at least one X-ray emitter for emitting X-rays, at least one X-ray sensor for receiving and/or detecting X-rays; and/or (vii) the first 3D structure comprises at least one model representing at least partly and/or at least in some areas at least one first dental object, in particular comprising at least one incisor, and/or the first jaw, and/or the second 3D structure comprises at least one model representing at least partly and/or at least in some areas at least one second dental object, in particular comprising at least one incisor and/or the second jaw.

It can also be preferred that the alignment, positioning and/or arrangement of the first and/or second 3D structure within the coordinate system assigned and/or assignable to the X-ray machine comprises the step: aligning, positioning and/or arranging the first 3D structure and/or the second 3D structure, in particular in a defined and/or definable manner, on and/or relative to at least one 3D auxiliary structure, wherein preferably at least one reference point is defined in the 3D auxiliary structure, in particular at least one positioning structure comprised by the 3D auxiliary structure, preferably at least one elevation and/or at least one recess, as a virtual patient position.

Advantageously, it is also possible that the 3D auxiliary structure has a known alignment, orientation and/or position within the coordinate system.

Furthermore, it can be provided that the alignment, positioning and/or arrangement of the first and/or second 3D structure on and/or relative to the 3D auxiliary structure comprises (i) the central and/or symmetrical alignment, positioning and/or arrangement of the first 3D structure and/or the second 3D structure relative to the 3D auxiliary structure, in particular within the coordinate system; (ii) the central and/or symmetrical positioning, alignment and/or arrangement of the first 3D structure and/or the second 3D structure by means of at least one midsagittal plane and/or at least one head/auditory canal holder; and/or (iii) the positioning, alignment and/or arrangement of the first 3D structure and/or the second 3D structure by means of the Frankfurt horizontal (FH) plane.

It is also preferred that the alignment, positioning and/or arrangement of the first and/or second 3D structure on and/or relative to the 3D auxiliary structure includes the alignment, positioning and/or arrangement of the first and/or second 3D structure by means of the reference point and/or by means of the model of an incisor comprised by the first and/or second 3D structure, in particular the arrangement of the incisor model, preferably by at least one cutting edge of the incisor, within the recess comprised by the 3D auxiliary structure, at least partially and/or at least in some areas.

Furthermore, it can be advantageous that the alignment, positioning and/or arrangement of the first and/or second 3D structure on and/or relative to the 3D auxiliary structure comprises the inclusion of at least one plane determined by the first 3D structure and/or the second 3D structure, wherein preferably the plane is determined essentially at least in some areas (a) by at least one first and/or second dental object, preferably a plurality of first and/or second dental objects, and/or (b) by at least one surface, in particular at least one occlusal surface, of at least one first and/or second dental object, preferably a plurality of first and/or second dental objects.

One embodiment can also be characterised in that the 3D auxiliary structure (a) comprises at least in some areas at least one area designed as a bite block and/or (b) corresponds at least partly and/or essentially at least in some areas to at least one model of at least one positioning unit, in particular in the form of at least one bite block, comprised at least partly by the X-ray machine, preferably the positioning unit being aligned, positioned and/or orientated relative to the X-ray machine in a known manner.

It is also proposed by the invention that the method also comprises the steps: calculating at least one 3D output structure comprising the first 3D structure, the second 3D structure, the 3D auxiliary structure and/or at least one 3D structure of at least one part of at least one, preferably generic and/or individual, especially saved, in particular in a data memory and/or retrieved and/or retrievable from there, head and/or skull; transmitting and/or outputting the 3D output structure, in particular on and/or to at least one display device preferably comprised by the X-ray machine; Taking, creating and/or calculating at least one X-ray image, preferably a 2D and/or 3D X-ray image, in particular by operating the X-ray machine and/or the movement unit according to the at least one parameter, in particular by performing the movement of the movement unit comprised by the X-ray machine along at least the section of the movement trajectory within the coordinate system; and/or transmitting and/or outputting the X-ray image, in particular on and/or to at least one display device, preferably comprised by the X-ray machine.

This objective is achieved according to a second aspect of the invention by a device for data processing, comprising means for carrying out the steps of the method according to the first aspect.

This objective is achieved according to a third aspect of the invention by a computer program product, comprising instructions which, when the program is executed by a computer and/or the device according to the second aspect, cause the computer and/or the device to carry out the steps of the method according to the first aspect.

This objective is achieved according to a fourth aspect of the invention by a computer-readable medium, comprising instructions which, when executed by a computer and/or the device according to the second aspect, cause the computer and/or the device to carry out the steps of the method according to the first aspect.

This objective is achieved according to a fifth aspect of the invention by an X-ray machine, comprising at least one positioning unit and at least one device according to the second aspect.

It is particularly preferred that (i) the positioning unit (a) has a known alignment, position and/or orientation relative to the X-ray machine, in particular within at least one coordinate system assigned and/or assignable to the X-ray machine, (b) is designed at least in some areas in the form of a bite block, (c) is fixed relative to the X-ray machine and/or (d) corresponds at least in some areas geometrically to the 3D auxiliary structure; and/or (ii) the X-ray machine further comprises at least one display device and/or at least one movement unit, wherein preferably the movement unit comprises at least one X-ray emitter for emitting X-rays, at least one X-ray sensor for receiving and/or detecting X-rays.

This objective is achieved according to a sixth aspect of the invention by a method for taking an X-ray image, which can be carried out by means of an X-ray machine, of at least one surface and/or volume area of at least one part of at least one head of at least one patient, wherein the method is preferably adapted to cooperate with a method according to the first aspect, comprising the steps: recording first data with respect to at least one area of at least one first anatomical structure of the head and/or recording second data with respect to at least one area of at least one second anatomical structure of the head; transmitting third data, by means of which the surface and/or volume area is determined and/or determinable at least in some areas within at least one coordinate system assigned and/or assignable to the X-ray machine; positioning, aligning and/or arranging the patient's head inside the X-ray machine; and activating the X-ray process.

It is particularly preferable here that the first data and/or the second data are recorded and/or recordable by means of at least one optical recording unit, in particular at least one intraoral camera, at least one laser-based measuring system and/or at least one camera, preferably at least one 3D camera, and/or the first data comprises at least image data of at least the occlusal surfaces of at least half the side of the upper jaw of the patient and/or the second data comprises at least image data of at least the occlusal surfaces of at least half the side of the lower jaw of the patient.

It is also possible that the surface and/or volume area is determined and/or determinable by means of at least one 3D output structure, preferably based on the first and/or second data.

It is also preferable that the method further comprises the steps: receiving at least one 3D output structure, in particular based on the first and second data; outputting the 3D output structure, in particular on at least one display device, preferably comprised by the X-ray machine; receiving the X-ray image; and/or outputting the X-ray image, in particular on at least one display device, preferably comprised by the X-ray machine.

Advantageously, it is also possible that the positioning, alignment and/or arrangement of the patient's head inside the X-ray machine preferably comprises (i) the positioning, alignment and/or arrangement of at least one incisor comprised by the patient's head, in particular an incisor of the upper jaw, in at least one positioning unit fixed relative to the X-ray machine, preferably centrally and/or in at least one positioning structure, preferably at least one elevation and/or at least one recess of the positioning unit, wherein the positioning unit is designed at least in some areas in the form of at least one bite block, preferably comprised by the X-ray machine and/or corresponds at least in some areas geometrically to the 3D auxiliary structure;

(ii) the central and/or symmetrical positioning, alignment and/or arrangement of the patient's head, in particular relative to the positioning unit, by means of at least one midsagittal plane and/or at least one head/auditory canal holder; and/or (iii) the positioning, alignment and/or arrangement of the patient's head, in particular relative to the positioning unit, by means of the Frankfurt horizontal (FH) plane.

It can preferably also be provided that (i) the first anatomical structure comprises at least one first jaw, at least one first dental object and/or at least one midface, in particular at least one frontal sinus cavity; (ii) the second anatomical structure comprises at least one second jaw, at least one second dental object and/or at least the midface, in particular the frontal sinus cavity; and/or (iii) the first jaw comprises and/or represents an upper jaw, the second jaw comprises and/or represents a lower jaw, in particular corresponding to the first jaw, the first dental object is arranged at least partly and/or at least in some areas in and/or on the first jaw, the second dental object is arranged at least partly and/or at least in some areas in and/or on the second jaw, the first dental object comprises at least one tooth, in particular of the first jaw, and/or the second dental object comprises at least one tooth, in particular of the second jaw.

Advantageously, it is also possible that (i) the first data and/or the second data are recorded and/or recordable by MRT, X-ray and/or at least one optical recording unit, in particular at least one intraoral camera, at least one laser-based measuring system and/or at least one camera, preferably at least one 3D camera; (ii) the first data comprises MRT data, X-ray data, optical image data, distance data, height data, reflection data, a virtual imprint and/or 3D data, in particular precalculated 3D data, with respect to the first anatomical structure, in particular the first jaw and/or the first dental object; (iii) the second data comprises MRT data, X-ray data, optical image data, distance data, height data, reflection data, a virtual imprint and/or 3D data, in particular precalculated 3D data, with respect to the second anatomical structure, in particular the second jaw and/or the second dental object; (iv) the first data comprises information on at least one surface, in particular at least one occlusal surface, of the first dental object and/or the first data comprises image data of at least the occlusal surfaces of at least half the side of the upper jaw of the patient; and/or (v) the second data comprises information on at least one surface, in particular at least one occlusal surface, of the second dental object and/or the second data comprises at least image data of at least the occlusal surfaces of at least half the side of the lower jaw of the patient.

The invention is thus based on the surprising finding that in a flexible manner and without additional radiation exposure the footprint area (FoV) of an X-ray machine can be adjusted to the region of interest (ROI), if the selection of the region of interest (ROI) is performed by means of at least one first and/or second 3D structure obtained preferably by means of another modality than X-ray, based on first and/or second data, representing at least partly the patient's head, provided that the first and/or second 3D structure is/are represented in a coordinate system assigned and/or assignable to the X-ray machine. The inventors have also recognised that first and/or second data obtained by X-ray can be used very advantageously, if the latter are available from earlier processes, for example, because there is namely no additional exposure to radiation.

By means of the common coordinate system, namely the first and/or second 3D structure is arrangeable virtually with respect to the alignment, orientation and/or position inside the X-ray machine in a known manner, and the area selected on the basis of the first and/or second 3D structure is transferable to a real surface and/or volume area detected or detectable by the X-ray machine. In other words, the 3D structure and the X-ray machine are thus spatially registered. If the patient in the X-ray machine and its associated model in the form of the first and/or second 3D structure are then essentially congruent the region of interest can be determined precisely by third data, by means of the first and/or second 3D structure.

In order to achieve said congruence the inventors have found surprisingly that preferably a 3D auxiliary structure can be provided which corresponds to a model of a positioning unit known precisely in terms of alignment, orientation and/or position which is comprised by the X-ray machine. Thus the first and/or second 3D structure is arrangeable on the 3D auxiliary structure and the patient's head is arrangeable on the positioning unit in the same manner and are thus congruent. For example, the 3D auxiliary structure can comprise a model of a bite block comprised by the X-ray machine.

The first 3D structure can preferably be a first anatomical structure of the head of the patient. The first anatomical structure thereby preferably comprises at least one first jaw, in particular an upper jaw, and/or at least one midface, in particular at least one frontal sinus cavity. Alternatively or in addition, first dental objects can also be part of the first anatomical structure and thus of the first 3D structure. Accordingly, the second 3D structure can preferably be a second anatomical structure of the head of the patient. The second anatomical structure thereby preferably comprises at least one second jaw, in particular a lower jaw, and/or at least the midface, in particular at least the frontal sinus cavity. Alternatively or in addition, second dental objects can also be part of the second anatomical structure and thus of the second 3D structure. A dental object within the meaning of this invention comprises for example one or more teeth and/or one or more tooth restorations.

The inventors have further found that a coinciding, thus congruent, alignment of the first and/or second 3D structure on the one hand and patient's head on the other hand can be produced with one or more of the following three points:

A cutting edge of the upper incisors might serve as a reference point of the patient, which cutting edge is located centrally in a recess of the positioning unit, for example in the form of a bite block. A cutting edge of the upper and/or lower incisors might also serve as a reference point in the first and/or second 3D structure, which cutting edge is located centrally in at least one recess of the 3D auxiliary structure designed at least in some areas as a bite block. In general however, each positioning structure comprised by the 3D auxiliary structure can be defined as a virtual patient position.

To determine the rotation about a vertical head axis and a left/right head inclination at the patient the head of the patient can be adjusted centrally and symmetrically by the midsagittal plane and/or the head/auditory canal holder. To determine the rotation about a vertical head axis and a left/right head inclination at the first and/or second 3D structure the 3D structures can be adjusted centrally and symmetrically at the 3D auxiliary structure, possibly also by incorporating the midsagittal plane.

To determine the forward/backward head inclination of the patient the head inclination can be adjusted by the Frankfurt horizontal (FH) plane. To determine the forward/backward inclination at the first and/or second 3D structure, the occlusal plane, in particular of the first jaw and/or the upper jaw, can be calculated from the first and/or second 3D structure. There is therefore a usable anatomical interrelation between the FH plane and the occlusal plane. In particular, this is about 9 degrees with small individual deviations. Alliteratively or in addition the FH plane can also be included directly in the 3D structures.

By means of these interrelations preferably a registration can be achieved. Preferably, by determining a ROI or corresponding third data, all geometrical details are known to the system and the required trajectories and X-ray parameters for an X-ray image can be calculated.

In other words, the inventors have thus found a solution to the aforementioned problem, for example in that the first and second 3D structure represent a virtual jaw imprint. The first and second data required for this are detected for example by means of a conventional 3D intraoral camera, which is guided through the oral cavity. Hereby preferably at least half the side of the occlusal surfaces of the upper and lower jaw are measured and are combined spatially into a virtual first and/or second 3D structure. The cutting edge of the upper and/or lower incisors can serve as a particularly marked reference point of the 3D structures and also of the real patient's head.

In particular, with a conventional bite block said cutting edge bites from above into a recess (which could also be referred to as a groove) of the bite block. Also for the 3D auxiliary structure a virtually modelled bite block can also preferably be provided which is used by means of its known, geometric design as a connecting piece to the X-ray machine and thus can be used for a spatial registration of the first 3D structure, the second 3D structure and alliteratively or in addition the 3D auxiliary structure and the X-ray machine. When the patient bites into the bite block, which corresponds to the virtual bite block of the 3D auxiliary structure, the incisors are located at the aforementioned reference point. Of course the "reference point" should not be taken literally, as, for example, the said cutting edge and recess mentioned by way of example can of course have a geometric extension, are thus not point-like. The real patient's head position (rotational angle) to the X-ray machine is adjusted often for example by the FH plane and midsagittal plane. The patient thus adopts a known basic position, which can be represented virtually as described above.

BRIEF DESCRIPTION OF THE DRAWINGS

Further features and advantages of the invention are given in the following description, in which preferred embodiments of the invention are explained by means of Figures.

In the latter.

DETAILED DESCRIPTION OF THE INVENTION

Figure 1:
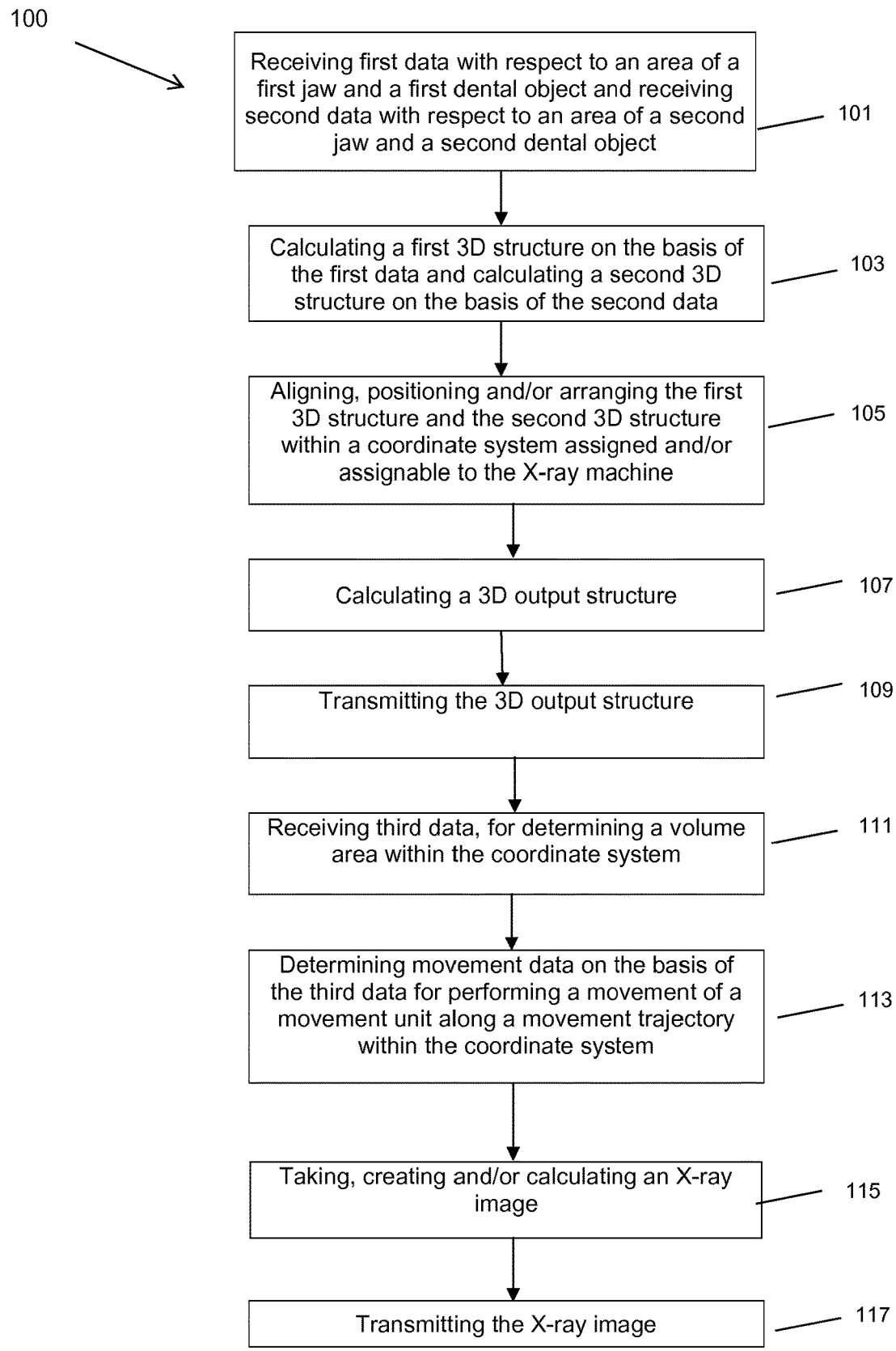
FIG. 1 is a flowchart of a method according to the first aspect of the invention.

FIG. 1 shows a flowchart 100 of a method according to the first aspect of the invention. By means of the method according to the flowchart 100 an X-ray image which can be carried out by means of an X-ray machine of at least one surface and/or volume area of at least one part of at least one head can be prepared.

In a step 101, first data with respect to an area of a first anatomical structure of the head in the form of a first jaw and at least one first dental object, and second data with respect to an area of a second anatomical structure of the head in the form of a second jaw and at least one second dental object is received. The first jaw is here an upper jaw and the second jaw a lower jaw corresponding to the upper jaw. The first dental objects thus comprise teeth of the upper jaw and the second dental objects comprise teeth of the lower jaw.

In a step 103, a first 3D structure at least of the area of the first jaw and the first dental object is calculated on the basis of the first data. In addition, a second 3D structure of the area of the second jaw and the second dental objects are calculated on the basis of the second data. In other words, a three-dimensional image of the first and second jaw and the dental objects is thus calculated, in particular to the extend the first and second data are provided.

In a step 105, the first 3D structure and the second 3D structure are aligned, positioned and/or arranged within a coordinate system assigned and/or assignable to the X-ray machine. In particular, for this purpose the first 3D structure and the second 3D structure are aligned, positioned and/or arranged in a defined manner at and relative to a 3D auxiliary structure. For this purpose for example an occlusal surface of at least a first and/or second dental object or the first and/or second 3D structure are also included. Alternatively or in addition, also the arrangement of an incisor model comprised by the first or second 3D structure within a recess comprised by the 3D auxiliary structure might be incorporated.

The 3D auxiliary structure has in turn within the coordinate system a known alignment, orientation and/or position and further corresponds to a model of a positioning unit comprised by the X-ray machine in the form of a bite block. While on the one hand the relative alignment, position and orientation of the real bite block relative to the X-ray machine are known and on the other hand the relative alignment, position and orientation of the first and second 3D structure relative to the 3D auxiliary structure in the coordinate system are also known by means of the known alignment, position and orientation of the 3D auxiliary structure in the coordinate system, it is possible to transfer the coordinate system to the X-ray machine.

Since the real bite block relative to the X-ray machine is known, it is possible to assign the coordinate system to the X-ray machine by means of the 3D auxiliary structure corresponding to the bite block. Ultimately, in this way it is thus possible to arrange the first and/or second 3D structure, so to speak, virtually inside the X-ray machine.

In other words the first 3D structure is linked via the virtual bite block to the coordinates of the X-ray machine. Thus, for example, by arranging the incisor in the recess. Afterwards the second 3D structure is docked, so to speak, to the first 3D structure.

Figure 2:
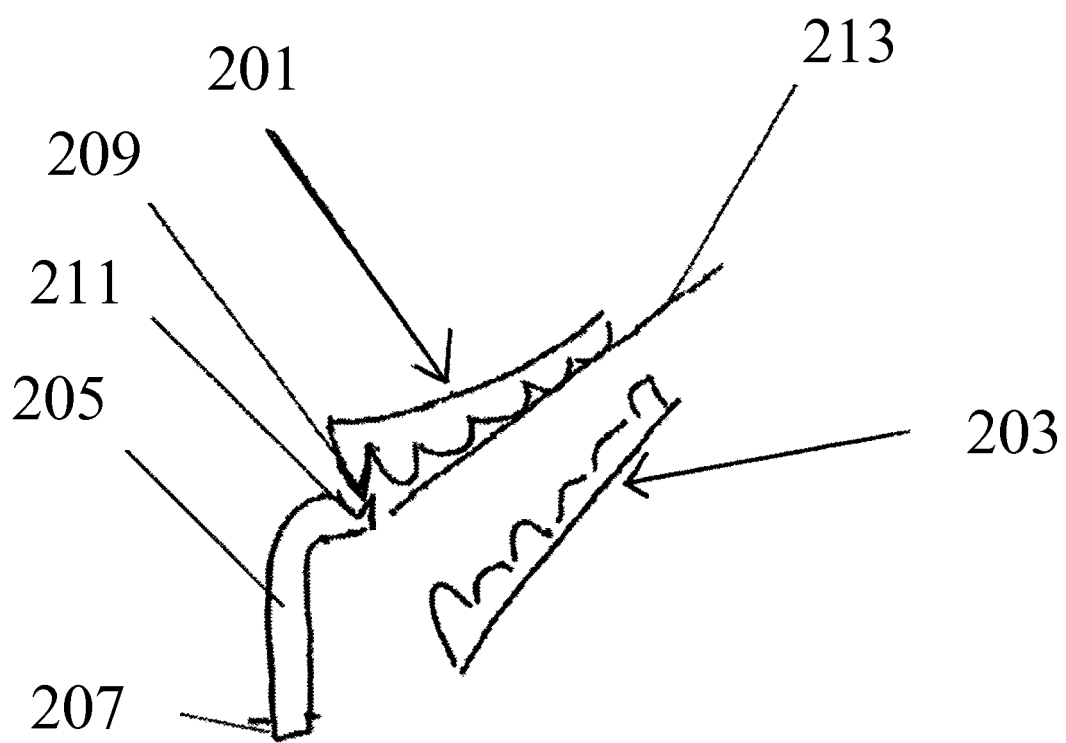
FIG. 2 is an illustration of a first and second 3D structure with a 3D auxiliary structure.

FIG. 2 shows in this context an illustration of a first 3D structure 201 in the form of an upper jaw with dental objects in the form of teeth and a second 3D structure 203 in the form of a lower jaw with dental objects in the form of teeth. The first and second 3D structure 201,203 are arranged relative to a 3D auxiliary structure 205 in the form of a bite block. The positioning unit of the X-ray machine corresponding to the 3D auxiliary structure 205 is connected at a reference point 207 to the X-ray machine. An incisor 209 of the first 3D structure 201 is arranged in a recess 211 of the 3D auxiliary structure 205. By means of the first 3D structure 201 a first occlusal plane 213 can also be defined.

In a step 107 a 3D output structure comprising the first 3D structure, the second 3D structure, the 3D auxiliary structure and a 3D structure of a generic head is calculated.

In a step 109 the 3D output structure is transmitted.

In a step 111 third data is received, by means of which the surface and/or volume area within the coordinate system is determined and/or determinable at least in some areas. The third data thus determines from which surface and/or volume area the X-ray image is to be taken.

In a step 113 parameters of the X-ray machine in the form of movement data for performing a movement of a movement unit comprised by the X-ray machine along a movement trajectory within the coordinate system is determined on the basis of the third data. The movement unit thereby comprises an X-ray transmitter for transmitting X-rays and an X-ray sensor for receiving and/or detecting X-rays. In other words, a movement of the movement unit is determined, by means of which the surface and/or volume area can be recorded according to the third data.

In a step 115 an X-ray image is taken, created and/or calculated by performing the movement of the movement unit comprised by the X-ray machine along the movement trajectory.

In a step 117 the X-ray image is transmitted.

Figure 3:
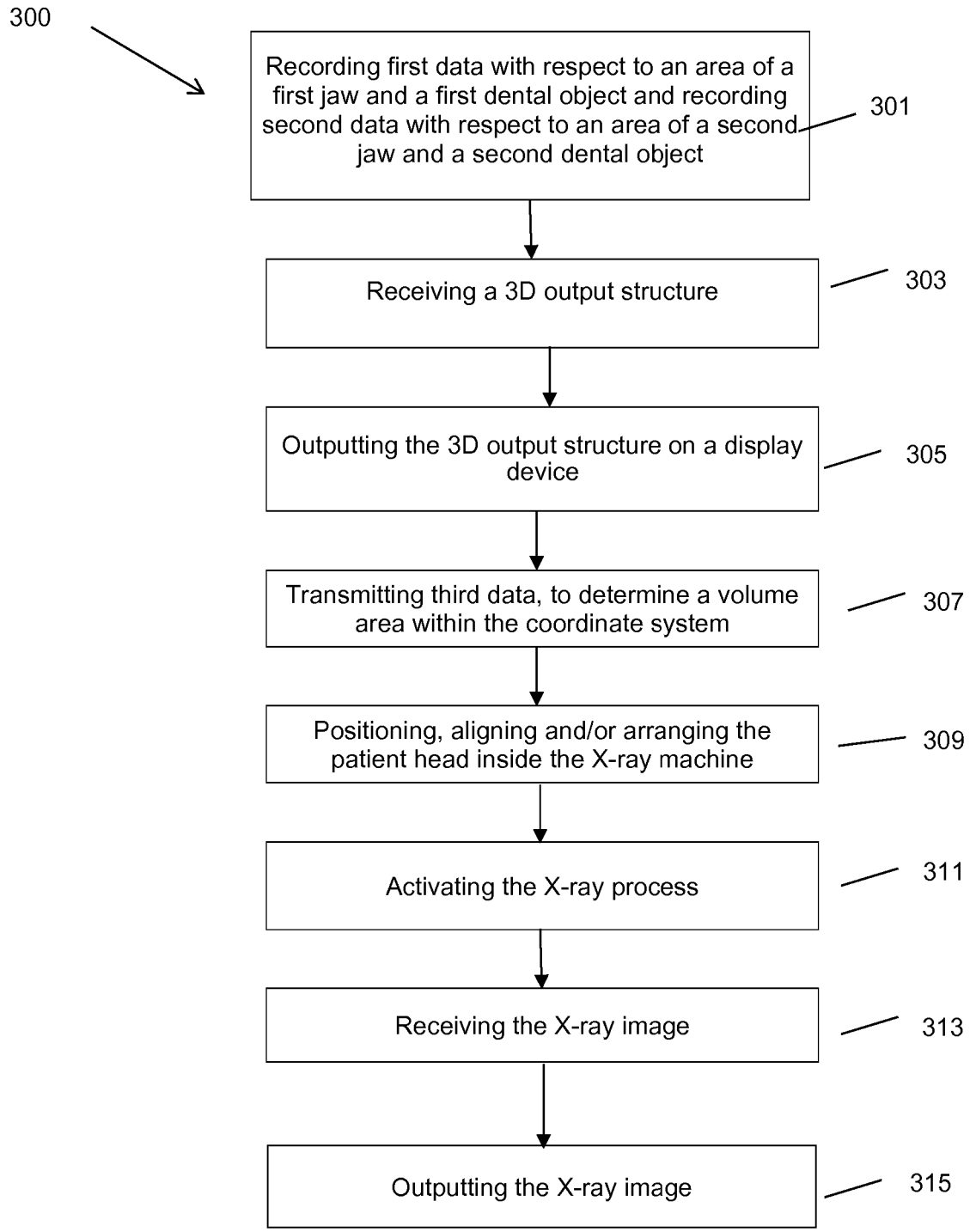
FIG. 3 is a flowchart of a method according to the sixth aspect of the invention.

FIG. 3 shows a flowchart 300 of a method according to the sixth aspect of the invention. By means of the method according to the flowchart 300 an X-ray image is taken which can be carried out by an X-ray machine of a surface and/or volume area of a head of a patient.

In a step 301, first data with respect to an area of a first anatomical structure of the head in the form of a first jaw and at least one first dental object and second data with respect to an area of a second anatomical structure of the head in the form of a second jaw and at least one second dental objects are recorded. The first jaw is here an upper jaw and the second jaw is a lower jaw corresponding to the upper jaw. The first dental objects thereby comprise teeth of the upper jaw and the second dental objects comprise teeth of the lower jaw. In other words, the oral cavity is measured in 3D by an intraoral 3D camera, for example.

In a step 303 a 3D output structure is received. This is based on the first and second data.

In a step 305 the 3D output structure is outputted on a display device.

In a step 307 third data is transmitted, by means of which the surface and/or volume area is determined within a coordinate system assigned and/or assignable to the X-ray machine. The third data thus determines from which surface and/or volume area the X-ray image is to be taken. In other words, the Region of interest (ROI) is determined, in particular by the user.

Figure 4:
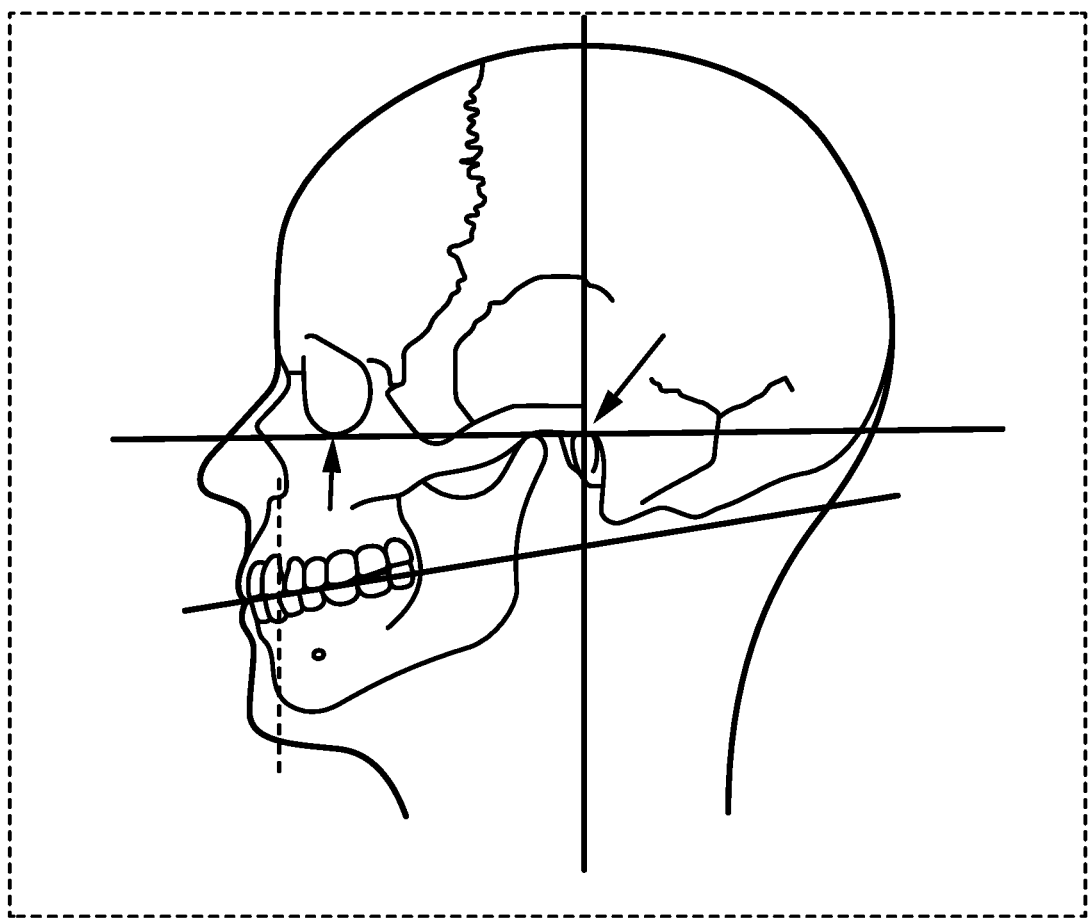
FIG. 4 shows a representation of a head.

In a step 309 the patient's head is positioned, aligned and/or arranged inside the X-ray machine. This comprises positioning and/or arranging at least one incisor of the patient's head, in particular an incisor of the upper jaw, in a recess of a positioning unit which is fixed relative to the X-ray machine. Furthermore, alternatively or in addition the midsagittal plane, at least one head/auditory canal holder and/or the Frankfurt horizontal plane (FH) are also incorporated. In other words, the patient bites into the bite block (reference point) and the head is aligned on the Frankfurt horizontal plane and midsagittal plane. FIG. 4 shows in particular the course of the FH plane for a head.

In a step 311 the X-ray process is activated.

In a step 313 the X-ray image is received.

In a step 315 the X-ray image is outputted on a display device.

The features disclosed in this description, the claims and the figures form the basis of the claimed invention, both individually and also in any combinations, for the respective different embodiments.

List of Reference Numerals 100 flowchart
101-117 step
201 3D structure
203 3D structure
205 3D auxiliary structure
207 reference point
209 dental object
211 recess
213 plane
300 flowchart
301-315 step

The invention claimed is:

1. A method for preparing an X-ray image, winch can be carried out by means of an X-ray machine comprising positioning unit, of at least one surface and/or volume area of a part of a head of at least one patient, comprising the steps:
receiving and/or processing first data with respect to at least one area of a first anatomical structure of the head;
calculating a first 3D structure of the area of the first anatomical structure on the basis of the first data;
providing a 3D auxiliary structure which corresponds to a model of said positioning unit and of known alignment, orientation and/or position within a coordinate system assigned and/or assignable to the machine;
aligning, positioning and/or arranging by means of said 3D auxiliary structure, the first 3D structure within said coordinate system assigned and/or assignable to the X-ray machine;
receiving and/or processing third data;
determining, by means of the third data, the surface and or volume area within the coordinate system, from which surface and/or volume area an X-ray image is to be taken; and
determining, on the basis of at least the third data, at least one parameter for operating the X-ray machine.

2. The method according to claim 1, wherein
(i) the first anatomical structure comprises at least one first jaw, at least one first dental object and/or at least one midface, in particular at least one frontal sinus cavity;
(ii) receiving and/or processing second data with respect to at least one area of a second anatomical structure of the head, this second anatomical structure comprises at least one second jaw, at least one second dental object and/or at least the midface, in particular the frontal sinus cavity;
(iii) calculating at least one second 3D structure at least of the area of the second anatomical structure on the basis of at least the second data;
(iv) the first jaw comprises and/or represents an upper jaw, the second jaw comprises and/or represents a lower jaw, in particular corresponding to the first jaw, the first dental object is arranged at least partly and/or at least in some areas in and/or on the first jaw, the second dental object is arranged at least partly and/or at least in some areas in and/or on the second jaw, the first dental object comprises at least one tooth, in particular of the first jaw, and/or the second dental object comprises at least one tooth, in particular of the second jaw;
(v) the third data (a) is predefined, in particular saved in a storage unit and is preferably retrieved from the latter, (b) is selected and/or can be selected by a user, in particular textually and/or graphically, and/or (c) is selected and/or can be selected by means of segmentation and/or artificial intelligence, in particular by a computer device; and/or
(vi) the parameter comprises and/or represents (a) setting data for setting at least one aperture, in particular comprised by the X-ray machine, (b) setting data for setting at least one dose of X-rays used by the X-ray machine and/or (c) movement data for performing at least one movement of the movement unit along at least one section of at least one movement trajectory within the coordinate system.

3. The method according to wherein
(i) the first data and/or the second data are recorded and/or recordable by MRT, X-ray and/or at least one optical recording unit, in particular at least one intraoral camera, at least one laser-based measuring system and/or at least one camera, preferably at least one 3D camera;
(ii) the first data comprises MRT data, X-ray data, optical image data, distance data, height data, reflection data, a virtual imprint and/or 3D data, in particular precalculated 3D data, with respect to the first anatomical structure, in particular the first jaw and/or the first dental object;
(iii) the second data comprises MRT data, X-ray data, optical image data, distance data, height data, reflection data, a virtual imprint and/or 3D data, in particular precalculated 3D data, with respect to the second anatomical structure, in particular the second jaw and/or the second dental object;
(iv) the first data comprises information on at least one surface, in particular at least one occlusal surface, of the first dental object and/or the first data. comprises image data of at least the occlusal surfaces at least of half the side of the upper jaw of the patient;
(v) the second data comprises information on at least one surface, in particular at least one occlusal surface, of the second dental object and/or the second data comprises at least image data of at least the occlusal surfaces of at least half the side of the lower jaw of the patient;
(vi) the movement unit comprises at least one X-ray emitter for emitting X-rays, at least one X-ray sensor for receiving and/or detecting X-rays;
and/or (vii) the first 3D structure comprises at least one model representing at least partly and/or at least in some areas at least one first dental object, in particular comprising at least one incisor, and/or the first jaw, and/or the second 3D structure comprises at least one model representing at least partly and/or at least in some areas at least one second dental object, in particular comprising at least one incisor, and/or the second jaw.

4. The method according to claim 1, wherein the alignment, positioning and/or arrangement of the first and/or second 3D structure within coordinate system assigned and/or assignable to the X-ray machine comprises the step:

aligning, positioning and/or arranging the first 3D structure and/or the second 3D structure, in particular in a defined and/or definable manner, on and/or relative to at least one 3D auxiliary structure, wherein preferably at least one reference point is defined in the 3D auxiliary structure, in particular at least one positioning structure comprised by the 3D auxiliary structure preferably at least one elevation and/or at least one recess, as a virtual patient position.

5. The method according to claim 4, wherein the 3D auxiliary structure has a known alignment, orientation and/or position within the coordinate system.

6. The method according to any of claims 4, wherein the alignment, positioning and/or arrangement of the first and/or second 3D structure on and/or relative to the 3D auxiliary structure comprises (i) the central and/or symmetrical alignment, positioning and/or arrangement of the first 3D structure and/or the second 3D structure relative to the 3D auxiliary structure in particular within the coordinate system;

(ii) the central and/or symmetrical positioning, alignment and/or arrangement of the first 3D structure and/or the second 3D structure by means of at least one midsagittal plane and/or at least one head/auditory canal holder;

and/or (iii) the positioning, alignment and/or arrangement of the first 3D structure and/or the second 3D structure by means of the Frankfurt horizontal (FH) plane.

7. The method according to any of claims 4, wherein the alignment, positioning and/or arrangement of the first and/or second 3D structure on and/or relative to the 3D auxiliary structure includes the alignment, positioning and/or arrangement of the first and/or second 3D structure by means of the reference point and/or by means of the model of an incisor comprised by the first and/or second 3D structure, in particular the arrangement of the incisor model, preferably by at least one cutting edge of the incisor, within the recess comprised by the 3D auxiliary structure, at least partially and/or at least in some areas.

8. The method according to any of claims 4, wherein the alignment, positioning and/or arrangement of the first and/or second 3D structure on and/or relative to the 3D auxiliary structure comprises the inclusion of at least one plane determined by the first 3D structure and/or the second 3D structure, wherein preferably the plane is determined essentially at least in some areas (a) by at least one first and/or second dental object, preferably a plurality of first and/or second dental objects, and/or (b) by at least one surface, in particular at least one occlusal surface, of at least one first and/or second dental object, preferably a plurality of first and/or second dental objects.

9. The method according to any of claims 4, wherein the 3D auxiliary structure (a) comprises at least in some areas at least one area designed as a bite block and/or (b) corresponds at least partly and/or essentially at least in some areas to at least one model of at least one positioning unit, in particular in the form of at least one bite block, comprised at least partly by the X-ray machine, preferably the positioning unit being aligned, positioned and/or orientated relative to the X-ray machine in a. known manner.

10. The method according to claim 1, wherein the method also comprises the steps:

calculating at least one 3D output, structure comprising the first 3D structure the second 3D structure, the 3D auxiliary structure and/or at least one 3D structure of at least one part of at least one, preferably generic and/or individual, especially saved, in particular in a data memory and/or retrieved and/or retrievable from there, head and/or skull.

transmitting and/or outputting the 3D output structure, in particular on and/or to at least one display device, preferably comprised by the X-ray machine;

taking, creating and/or calculating at least one X-ray image, preferably a 2D and/or 3D X-ray image, in particular by operating the X-ray machine and/or the movement unit according to the at least one parameter, in particular by performing the movement of the movement unit comprised by the X-ray machine along at least the section of the movement trajectory within the coordinate system;

and/or transmitting and/or outputting the X-ray image, in particular on and/or to at least one display device, preferably comprised by the X-ray machine.

11. A device for data processing, comprising means for carrying out the steps of the method of claim 1.

12. A computer program product, comprising instructions which, when executed by a computer and/or the device according to claim 11, cause the computer and/or the device to carry out the steps of the method according to claim 1.

13. A computer-readable medium, comprising instructions which when executed by a computer and/or the device according to claim 11 cause the computer and/or the device to carry out the steps of the method according to claim 1.

14. An X-ray machine, comprising at least one positioning unit and at least one device according to claim 11.

15. The X-ray machine according to claim 14, wherein (i) the positioning unit (a) has a known alignment, position and/or orientation relative to the X-ray machine, in particular within at least one coordinate system assigned and/or assignable to the X-ray machine, (b) is designed at least in some areas in the form of a bite block, (c) is fixed relative to the X-ray machine and/or (d) corresponds at least in some areas geometrically to the 3D auxiliary structure;

and/or (ii) the X-ray machine further comprises at least one display device and/or at least one movement unit, wherein preferably the movement unit comprises at least one X-ray emitter for emitting X-rays, at least one X-ray sensor for receiving and/or detecting X-rays.

* * * * *

UNITED STATES PATENT AND TRADEMARK OFFICE
CERTIFICATE OF CORRECTION

Page 1 of 2

PATENT NO. : 11,957,494 B2
APPLICATION NO. : 17/311412
DATED : April 16, 2024
INVENTOR(S) : Ulrich Schulze-Ganzlin It is certified that error appears in the above-identified patent and that said Letters Patent is hereby corrected as shown below:

In the Claims

In Column 11, Line 39, in Claim 1, delete "winch" and insert --which-- therefor

In Column 12, Line 35, in Claim 3, after "according to", insert --claim 1,--

In Column 12, Line 55, in Claim 3, delete "data." and insert --data-- therefor

In Column 12, Line 66, in Claim 3, after "X-rays;", delete a linebreak

In Column 13, Line 11, in Claim 4, after "within", insert --the--

In Column 13, Line 19, in Claim 4, after "structure", insert --,--

In Column 13, Line 25, in Claim 6, delete "any of claims" and insert --claim-- therefor In Column 13, Line 28, in Claim 6, after "comprises", insert a linebreak In Column 13, Line 31, in Claim 6, after "structure", insert --,--

In Column 13, Line 37, in Claim 6, after "holder;", delete a linebreak

In Column 13, Line 42, in Claim 7, delete "any of claims" and insert --claim-- therefor In Column 13, Line 53, in Claim 8, delete "any of claims" and insert --claim-- therefor In Column 14, Line 1, in Claim 9, delete "any of claims" and insert --claim-- therefor In Column 14, Line 9, in Claim 9, delete "a." and insert --a-- therefor Signed and Sealed this
Twenty-fourth Day of June, 2025

Coke Morgan Stewart
*Acting Director of the United States Patent and Trademark Office*

CERTIFICATE OF CORRECTION (continued)
U.S. Pat. No. 11,957,494 B2

In Column 14, Line 12, in Claim 10, delete "output," and insert --output-- therefor In Column 14, Line 18, in Claim 10, delete "skull." and insert --skull;-- therefor In Column 14, Line 30, in Claim 10, after "system;", delete a linebreak In Column 14, Lines 42-43, in Claim 13, after "instructions", insert --,--

In Column 14, Line 56, in Claim 15, after "structure;", delete a linebreak